United States Patent
Spotorno et al.

(10) Patent No.: US 6,179,842 B1
(45) Date of Patent: Jan. 30, 2001

(54) BLOCKING SYSTEM FOR THE MEDULLARY CANAL OF A TUBULAR BONE

(75) Inventors: Lorenzo Spotorno, Finale Ligure (IT); Willi Frick, Wabern; Mathias Heller, Winterthur, both of (CH)

(73) Assignee: Sulzer Orthopaedie AG, Baar (CH)

( * ) Notice: Under 35 U.S.C. 154(b), the term of this patent shall be extended for 0 days.

(21) Appl. No.: 09/337,801

(22) Filed: Jun. 22, 1999

(30) Foreign Application Priority Data

Jul. 2, 1998 (EP) .................................. 98810620

(51) Int. Cl.$^7$ .................................. A61B 17/58
(52) U.S. Cl. .................................. 606/95
(58) Field of Search .................. 606/95, 62, 92, 606/60, 93, 94, 86

(56) References Cited

U.S. PATENT DOCUMENTS

| 4,245,359 | 1/1981 | Stuhmer . |
|---|---|---|
| 4,293,962 | 10/1981 | Fuson . |
| 4,344,190 | 8/1982 | Lee . |
| 4,627,434 | 12/1986 | Murray . |
| 4,865,609 | 9/1989 | Roche . |
| 5,006,071 | 4/1991 | Carter . |
| 5,314,493 | 5/1994 | Mikhail . |

FOREIGN PATENT DOCUMENTS

| 3314210A1 | 1/1984 | (DE) . |
|---|---|---|
| 87 17 349 U | 2/1989 | (DE) . |
| 0143847 | 6/1985 | (EP) . |
| 0338981A1 | 10/1989 | (EP) . |
| 0652016A1 | 5/1995 | (EP) . |
| 2708192 | 2/1995 | (FR) . |
| WO 94/01063 | 1/1994 | (WO) . |
| WO 95/34331 | 12/1995 | (WO) . |
| WO 97/25940 | 7/1997 | (WO) . |

*Primary Examiner*—Michael Buiz
*Assistant Examiner*—Anthony S. King
(74) *Attorney, Agent, or Firm*—Townsend and Townsend and Crew LLP

(57) ABSTRACT

With the invention blocking systems for the medullary canal (1) of a tubular bone (2) are shown which have a blocking element (5) in order to hold bone cement (3) back from cemented prosthesis shafts (4). Because a deformable plug (6) which can be decomposed in the body is placed on between the blocking element (15) and the shaft end (7), which prevents an advance of liquid bone cement (3) in the capacity of a fill-in and which permits a penetration of the end (7) of the prosthesis shaft (4), a cement socket without a base arises which permits settling movements of the shaft in the hardened bone cement.

15 Claims, 2 Drawing Sheets

BLOCKING SYSTEM FOR THE MEDULLARY CANAL OF A TUBULAR BONE

BACKGROUND OF THE INVENTION

The invention relates to a blocking system for the medullary canal of a tubular bone in which a prosthesis shaft can be fastened with bone cement, with the blocking system having a blocking element which can be anchored in the medullary space prior to the introduction of the bone cement in order to prevent an advance of bone cement.

The previous teaching for the formation of the cement jacket about the shaft of a cemented in prosthesis starts from as uniformly thick a cement jacket as possible which completely surrounds the shaft, with at most a somewhat greater accumulation of bone cement being tolerated under the shaft end in order to compensate the fluctuations between the setting depth of a mechanical medullary space blocking and the penetration depth of the shaft end.

A mechanical medullary space blocking of this kind is described in the patent specification U.S. Pat. No. 4,293,962 with an associated setting tool. A similar medullary space blocking is shown by the patent specification U.S. Pat. No. 4,245,359 or U.S. Pat. No. 4,344,190 in which the material of the mechanical medullary space blocking can be decomposed in the body. A disadvantage of an arrangement of this kind consists in that relatively large drawing tensions can arise in the transition from the cement socket to the cement plug lying under the shaft end when the shaft moves slightly downwards within the hardened cement socket.

SUMMARY OF THE INVENTION

The object of the present invention is to keep the drawing tension small in the direction of the shaft prosthesis in the lower region of the cement socket. This object is satisfied in that a plug of a deformable material is placed on the blocking element which prevents an advance of liquid bone cement in the capacity of a fill-in or dummy and which permits a penetration of the end of the prosthesis shaft.

An advantage of this arrangement consists in that the shaft end can sink slightly within the tube-shaped socket in accordance with the creep movements of bone cement. Furthermore, there is no cement plug present which can come off or be pushed away to one side as a result of such a creep movement. Also, there is no cement plug present which must be tediously removed in a re-operation. In addition a greater accumulation of bone cement is avoided without it being necessary to observe narrower tolerances between the mechanical medullary space blocking and the shaft end. Because the plug is deformable between the shaft end and the mechanical medullary space blocking, the shaft tip can penetrate, while the still flowable bone cement is displaced backwards. Since the plug is still deformable even after the hardening of the bone cement, it can follow slight sinkings of the shaft, with the cement socket which is supported in the bone being pressed together more strongly. The increase of the drawing tension which extends around in ring shape in the lower socket turns out in this situation to be low, since a small axial sinking of the shaft causes a substantially lesser enlargement of the diameter due to the weak cone angle, which is on the order of magnitude of a few degrees.

A further advantage is present when the deformable plug decomposes in the body and in this manner the body's own tissue can grow in up to the end of the shaft in the form of bone marrow and fat. If the material of the blocking element also decomposes in the body in the medium term, no more parts which are foreign to the body are present beneath the shaft end by the dimensions of which a re-operation shaft would have to be set more deeply. In addition, in a re-operation a removal of the tubular cement socket is considerably simpler after the removal of the shaft which protrudes beyond the socket. Furthermore, it is prevented with this arrangement that a hitherto usual cement plug is torn off from one side of the socket and wanders under the slowly sinking shaft laterally into the tubular bone and weakens the latter. The deformable plug can consist of a plastically deformable, gelatinous or pasty material which gives way while largely preserving its volume when a shaft tip penetrates therein. It can however also consist of a foamed material, the volume of which collapses at the location of the penetration of a solid object. This does not exclude that the foamed plug has a certain elasticity, which permits it, compressed to a smaller diameter, to be introduced with a setting apparatus into a medullary canal where it can assume a larger diameter after being deposited. If a foam is used which easily solidifies on being released, then a plug of this kind can be deposited directly onto the blocking element with a spray can and an extension tube in this manner and can be used as the mentioned fill-in after a corresponding solidification. Hydrolysable materials containing gelatine can be decomposed in the body within hours to days. There are likewise bio-absorbable materials which the body can decompose with its enzymes in days to weeks so that it is possible with such plugs to have a space beneath the shaft immediately after the operation which permits a sinking of the shaft corresponding to the creep movements in the cement socket, at the latest during the first loading attempts, without additional loading peaks arising at the socket and at the transition from the latter to the supporting bone tissue.

The deformable plug must be applied to the blocking element as a fill-in prior to the introduction of the bone cement. A plastically deformable plug can also be positioned together with a mechanical medullary space blocking by a setting apparatus and then be uniformly distributed with a stopper. It is however also possible to lower a deformable plug using a separate setting apparatus and to thrust it out with a piston. It is likewise possible to surround the plastically deformable plug with a membrane which is elastic and can be decomposed in the body in order that it can be pushed into the medullary space in the form of an elongate cartridge and occupies the cross-section of the medullary space with respect to the following bone cement when it arrives at the mechanical medullary space blocking. Because the pressure of the bone cement on the plastically deformable plug is equally large everywhere, the latter experiences no substantial change of form, but merely lies everywhere in contact with the same pressure, whereas the shaft which follows outwardly displaces first the bone cement and then the mass of the plastic plug. In the use of a membrane about the plug it can be advantageous to provide the end of the shaft with a point. This can be pushed on or be a component of the shaft in order to puncture open the membrane.

DESCRIPTION OF THE SPECIFIC EMBODIMENT

Figure 1:
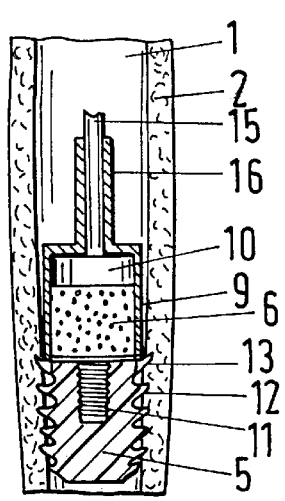
FIG. 1 shows schematically in a longitudinal section a setting apparatus with which a deformable plug can be deposited on a mechanical medullary space blocking in a tubular bone.

The figures show blocking systems for the medullary canal 1 of a tubular bone 2 which has a blocking element 5 in order to hold back bone cement 3 from cemented prosthesis shafts 4. Since a deformable plug 6 which prevents an advance of liquid bone cement 3 in the capacity of a fill-in and which permits a penetration by the end 7 of the prosthesis shaft is placed on between the blocking element 5 and the shaft end 7, a cement socket without a base arises, which permits settling movements of the shaft in the hardened bone cement.

In the following examples the same reference symbols are used for similar function elements.

Figure 2:
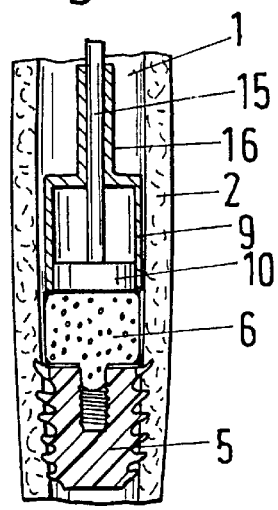
FIG. 2 shows schematically the arrangement of FIG. 1 during the ejection and pressing on of a deformable plug.
Figure 3:
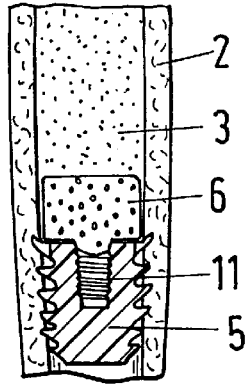
FIG. 3 shows schematically the arrangement of FIG. 2 after the setting apparatus has been moved out and after the filling with flowable bone cement.

In FIGS. 1 to 3 the function of a setting tool 10, 15, 16 is shown for a deformable plug 6. This deformable plug 6 consists of a plastically deformable material which can be decomposed in the human body, with it being possible for this decomposition to take place through disintegration as in hydrolysable gelatines and/or through the absorption of pasty bio-absorbable materials. The setting tool has a cylinder 9 which is continued as a sleeve 16 and takes up an ejection piston 10 with a piston rod 15. In the retracted state of the piston 10 the plug is punched out by the cylinder 9 as if from a cookie dough and deposited on (FIG. 1) and pressed onto (FIG. 2) a mechanical medullary space blocking 5. The end surface of the piston 10 and the cylinder wall 9 form a planar pressing surface. Subsequently liquid bone cement 3 can lie in contact above the plug 6, with the plug 6 screening the blocking element 5 in the capacity of a fill-in. The blocking element 5 has a plurality of peripherally extending ribs 12 and protruding elastic spikes 13 which permit an anchoring in a prepared medullary canal. A thread 11 is provided in the center in order to be able to set the blocking element with a threaded rod.

Figure 4:
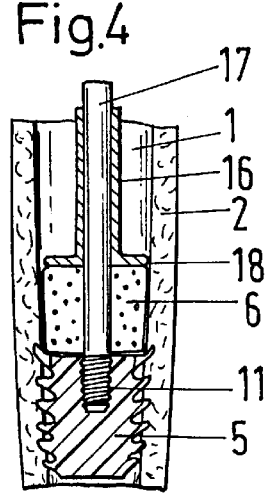
FIG. 4 shows schematically in a longitudinal section a setting apparatus for a mechanical medullary space blocking with a plastically deformable plug which is placed on in ring shape.
Figure 5:
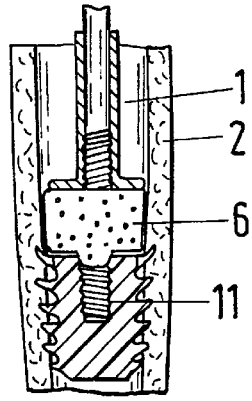
FIG. 5 shows schematically the arrangement of FIG. 4 during the pressing on of the plastically deformable plug at the anchored medullary space blocking.
Figure 6:
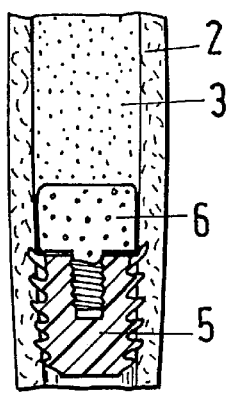
FIG. 6 shows schematically the arrangement of FIG. 5 after the setting apparatus has been moved out and after the filling in of flowable bone cement.

In FIGS. 4 to 6 is a combined setting tool 16, 17, 18 for a common setting of the blocking element 5 and of a ring-shaped plastically deformable plug 6. A threaded rod 17 protrudes through a guide sleeve 16 and is easily releasably screwed to the blocking element 5 via the thread 11. The sleeve 16 ends as a ring piston 18. The ring-shaped plug 6 is captured between the ring piston 18 and the blocking element 5 and can be introduced with the blocking element. After the setting the threaded rod is released from the blocking element and drawn back flush with the ring piston 18. The thus arisen piston surface is used for the pressing on of the ring-shaped plastic plug 6, which should still be sufficiently plastic that the central bore in the plug 6 is closed.

With FIG. 6 the same state as in FIG. 3 is then reached; the plug 6 acts as a fill-in between the bone cement 3 and the blocking element 5.

A further possibility of setting a plug 6 as a fill-in without a central bore consists in using a plug material which is elastically deformable in the manner of a finely porous sponge, with the pore size at the surface being so small that practically no bone cement penetrates. A "sponge" of this kind, which expands again after a pressing together, is deposited on a blocking element 5 in the compressed state with a setting apparatus 10, 15, 16 in accordance with FIGS. 1 and 2 and is pressed out in order to produce a fill-in against advancing bone cement. Its original diameter is so large that it lies in contact at the inner wall of the medullary canal 1.

Figure 16:
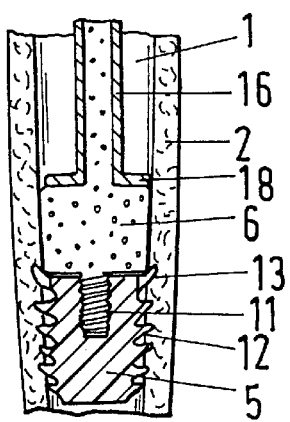
FIG. 16 shows schematically a filling apparatus in the form of a sleeve with a ring piston using which a foamed and solidifying plug can be applied to a mechanical medullary space blocking.

A plug 6 without a central bore can be produced directly on a blocking element 5 in accordance with FIG. 16 using a setting apparatus 16, 18 if a foam is used as a plug material which solidifies to such an extent that it withstands a slight pressure from the bone cement which is present over a large area, whereas it collapses at the point of incidence of a hard shaft end. The plug material, which is stored in a cartridge or a spray can, is deposited on a blocking element 5 via a tubelet 16 which enlarges in the shape of a ring 18. The setting apparatus 16, 18 is removed prior to the solidification of the foam in order that no bridges to the remaining foam arise in the tubelet 16. After the solidification the thus produced plug can prevent an advance of bone cement in the capacity of a fill-in, whereby a state such as in FIGS. 3 and 6 is achieved.

Figure 7:
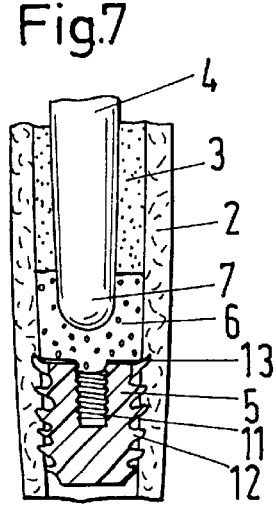
FIG. 7 shows schematically an arrangement in accordance with FIG. 3 or 6 in which a prosthesis shaft dips into the deformable plug.
Figure 8:
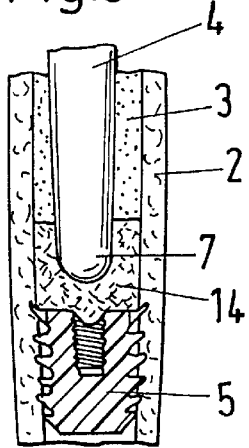
FIG. 8 shows schematically the arrangement of FIG. 7 in which the deformable plug is replaced by the body's own tissue.

A bone cement which lies in contact at the plug 6 in the liquid state (FIG. 3, FIG. 6) allows a lowering shaft end 7 to pass and to penetrate into the deformable plug as in FIG. 7. Depending on the kind of the plug 6 the latter reacts differently to the penetrating shaft end 7. The pasty, plastically deformable plug 6 gives way and passes on a developing pressure to the wetted surfaces in the manner of an enclosed liquid. Cavities such as the threaded bore 11 and the intermediate spaces between the elastic spikes 13 are still partially filled. The partition surface between the plug 6 and the bone cement 3 is displaced upwardly by the amount of the remaining volume which is displaced by the shaft end 7. In the case of a sponge-like plug material the plug material gives way elastically and settles about the penetrating shaft end under an increased bias force. An elastic, foamed plug 6 behaves in a similar manner. A rigid foamed plug 6, in contrast, collapses in the region of the penetrating shaft end 7 and holds back the bone cement 3 outside the shaft end. The material of the deformable plug 6 can be decomposed within a few hours to days by the body. In the event that hydrolysable gelatine is used as a plug material the plug 6 dissolves slowly in the body fluids and is distributed in the body. In the event that bio-absorbable substances are used as a plug material the plug 6 is likewise decomposed by the body's own enzymes within a few days to weeks, and a state in accordance with FIG. 8 arises in which the body's own liquid and cells 14 fill out the space between the shaft end 7 and the blocking element 5, whereas the socket of hardened bone cement 3 ends in the manner of a cut off tube. In this state the first loading attempts at the prosthesis shaft 7 are not very dangerous for the cement socket. No additional drawing tensions can build up via a cement plug extending about the shaft end, and a slight lowering of the shaft 4 and creep movements in the bone cement are still possible.

Figure 9:
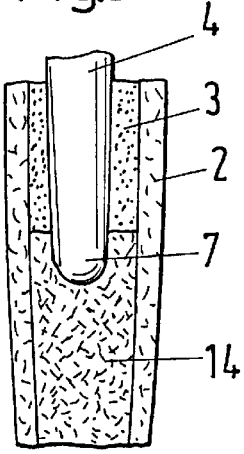
FIG. 9 shows schematically the arrangement of FIG. 7 in which the deformable plug and the mechanical medullary space blocking are replaced by the body's own tissue.

FIG. 9 shows the situation months later, when the blocking element, which contains bio-absorbable substances such as lactides, has disintegrated. The space about the shaft end 7 and beneath the shaft end is filled with the body's own tissue. A slight lowering of the shaft corresponding to the greater cone angles in the proximal region would not lead to inadmissible drawing tensions at the distal end of the socket of bone cement. If a re-operation becomes necessary later, the cement socket can be removed relatively easily after the loosening out of the shaft.

Figure 15:
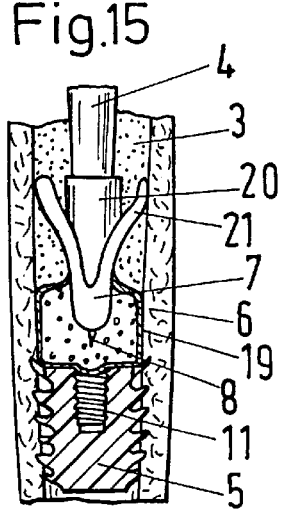
FIG. 15 shows schematically an arrangement analogous to FIG. 12 in which on a shaft a centering aid with a point has punctured the surrounding membrane and dips into the plastically deformable plug.
Figure 17:
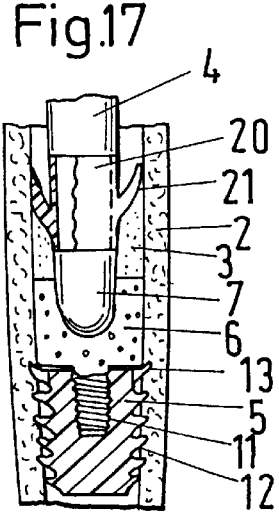
FIG. 17 shows schematically a shaft with a centering aid arranged in the lower third which leaves the shaft end free for a dipping in in the deformable plug.
Figure 18:
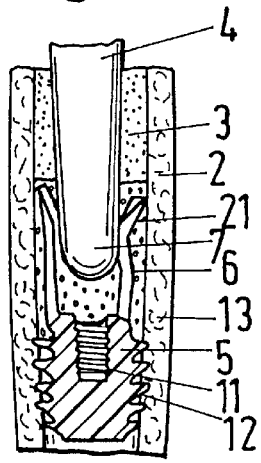
FIG. 18 shows schematically a mechanical medullary space blocking with a shaft centering in the form of arms which are arranged in the shape of a funnel and which protrude into a deformable plug.

FIGS. 15, 17 and 18 show arrangements of the invention in which a shaft 4 dips with its end 7 into a deformable plug 6 and at the same time experiences a centering within the medullary canal 1. In FIG. 15 the centering is solved in that the shaft 4 is extended by a centering aid 20 which can be pushed on and the end 7 of which protrudes into a deformable plug 6, the construction of which will be described later. Elastically resilient arms 21, by means of which the lower part of the shaft 4 is centered during the lowering into the medullary canal 1, stand off laterally from the centering aid 20. In the example shown the arms 21 are locate d in the region of the bone cement 3. If the deformable plug 6 is made with a corresponding height, the elastic arms 21 can also dip into the deformable plug, which can be of advantage when the centering aid also consists of a bio-absorbable material. The cement socket then experiences no interruptions through the arms 21.

The centering aid 20 of FIG. 17 consists of a thin-walled piece of tube of body-compatible plastic, which was pushed over the shaft end 7 and lies in contact in a puncture of the shaft 4 in order that a continuous contour of the shaft to the bone cement 3 is maintained. Merely at least three elastic arms 21 are provided which indirectly center the shaft end 7, which dips into the deformable plug. The examples of FIGS. 15 and 17 accept that the still liquid bone cement 3 is divided by the elastic arms 21 when the shaft 4 is lowered and must flow back together again behind the arms. This circumstance is circumvented in the example of the centering of FIG. 18. Elastic arms 21 which upwardly run out to the wall 2 of the medullary canal and which run together downwardly in the manner of a funnel and can capture and center a lowering shaft end 7 are attached there at the blocking element 5. The deformable plug 6 consists of a pasty, plastically deformable material which was introduced using a setting apparatus in accordance with FIG. 1 or FIG. 16 after the setting of the blocking element 12, 21 and pressed on through the elastic arms 21 in such an amount that the elastic arms 21 are completely covered. After the filling in of bone cement 3 the shaft 4 is lowered, with its tip 7 being captured via the elastic arms 21 and centered. The shaft end 7 dips relatively far and into the plastically deformable plug in order that a long centering path is present and a correspondingly large volume of liquid bone cement is upwardly displaced over the plug material in order to compensate the transverse displacement of the shaft axis in the bone cement which is connected with the centering through the necessarily upwardly flowing bone cement.

Figure 10:
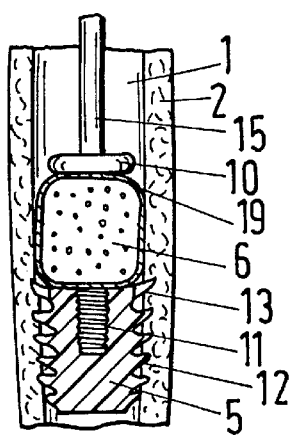
FIG. 10 shows schematically in a longitudinal section a plastically deformable plug with a surrounding membrane which is deposited on a mechanical medullary space blocking.
Figure 11:
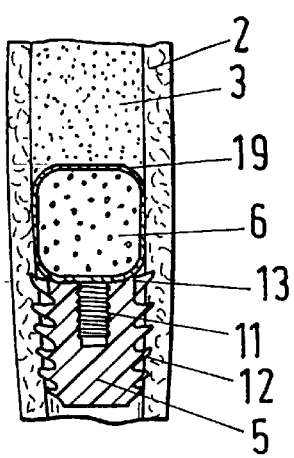
FIG. 11 shows schematically the arrangement of FIG. 10 after the filling in of flowable bone cement.
Figure 12:
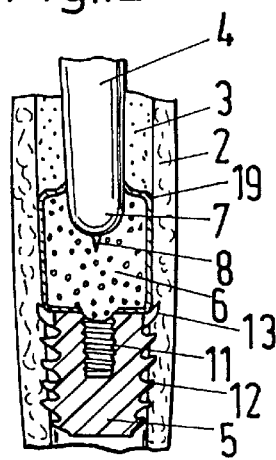
FIG. 12 shows schematically the arrangement of FIG. 11 in which a prosthesis shaft with a point has punctured the surrounding membrane and dips into the plastically deformable plug.
Figure 13:
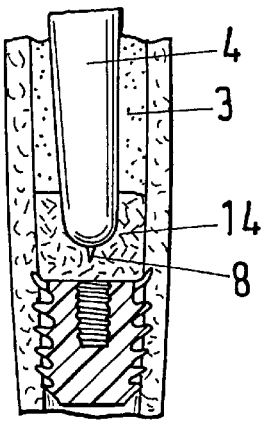
FIG. 13 shows schematically the arrangement of FIG. 12 in which the plastically deformable plug is replaced by the body's own tissue.
Figure 14:
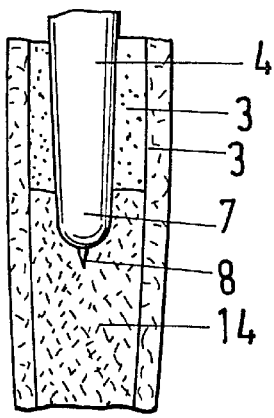
FIG. 14 shows schematically the arrangement of FIG. 12 in which the plastically deformable plug and the mechanical medullary space blocking are replaced by the body's own tissue.

FIGS. 10, 11, 12, 13, 14 and 15 show examples of a plastically deformable plug 6 which is surrounded by an elastic membrane 19 and which has an elongate cartridge form prior to introduction into the medullary canal 1. After the incidence of the plug 6 at a blocking element 5 the latter is pressed on with a piston 10 via a piston rod 15 (FIG. 10). Then the still liquid bone cement 3 is filled in (FIG. 11). A shaft 4 which is lowered through the bone cement 3 is provided at its end 7 with a point 8 which penetrates through the membrane 19 into the plastically deformable body 6 and displaces its material. If this membrane is highly elastic, no point 8 is required, but rather the membrane 19 then wraps about the penetrating shaft end 7. The point 8 can be a constituent of the shaft 4. It can be pushed on at the distal end of a shaft as a point or it can be pushed on at the shaft 4 as a constituent of a push-on centering aid 20 (FIG. 15). FIGS. 13 and 14 show, analogously to FIGS. 8 and 9, a shaft end with a point 8 which, in the case of materials for the plug 6 and the blocking element 5 which can be decomposed in the body, in the medium term represents the element which protrudes into the tubular bone the furthest.

What is claimed is:

1. A blocking system for the medullary canal of a tubular bone for fastening a prosthesis shaft with bone cement, the blocking system comprising:

a blocking element configured to be anchored in the medullary canal prior to introduction of the bone cement to prevent an advance of the bone cement, and a plug of a deformable material placed on the blocking element to prevent an advance of liquid bone cement in the capacity of a fill-in and to permit penetration of an end of the prosthesis shaft.

2. The blocking system of claim 1 wherein the deformable material of the plug is surrounded by an elastic membrane.

3. The blocking system of claim 2 wherein the elastic membrane is puncturable by a sharp point attached to an end of the prosthesis shaft.

4. The blocking system of claim 1 wherein the blocking element comprises a bio-absorbable material which is decomposable in a range of months in the human body.

5. The blocking system of claim 4 wherein the material of the blocking element includes lactides.

6. The blocking system of claim 1 wherein the deformable material of the plug is decomposable in the human body.

7. The blocking system of claim 1 wherein the plug comprises a material which is plastically deformable under pressure of a penetrating shaft end of the prosthesis shaft.

8. The blocking system of claim 1 wherein the plug comprises a foamed material which yields under pressure of a penetrating shaft end of the prosthesis shaft.

9. The blocking system of claim 1 wherein the plug is elastically deformable to a smaller volume.

10. The blocking system of claim 1 wherein the deformable material of the plug is decomposable in the human body in a range from hours to several days.

11. The blocking system of claim 1 wherein the deformable material of the plug comprises hydrolysable gelatine.

12. The blocking system of claim 1 wherein the deformable material of the plug comprises bio-absorbable constituents which are decomposable by the human body's own enzymes.

13. A setting apparatus for a blocking system for the medullary canal of a tubular bone for fastening a prosthesis shaft with bone cement, the blocking system comprising a blocking element configured to be anchored in the medullary canal prior to introduction of the bone cement to prevent an advance of the bone cement, and a plug of a deformable material placed on the blocking element to prevent an advance of liquid bone cement in the capacity of a fill-in and to permit penetration of an end of the prosthesis shaft, the setting apparatus comprising:

a cylindrical reception for the plug and an ejection piston which is journalled in the cylindrical reception for introducing the plug into the medullary canal.

14. The setting apparatus of claim 13 wherein the ejection piston includes a piston surface for pressing the plug against the blocking element.

15. A setting apparatus for a blocking system for the medullary canal of a tubular bone for fastening a prosthesis shaft with bone cement, the blocking system comprising a blocking element configured to be anchored in the medullary canal prior to introduction of the bone cement to prevent an advance of the bone cement, and a plug of a deformable material placed on the blocking element to prevent an advance of liquid bone cement in the capacity of a fill-in and to permit penetration of an end of the prosthesis shaft, the setting apparatus comprising:

a tubelet for introducing a still flowable plug onto the blocking element, with the plug material increasing in consistency so strongly after the introducing that no flowing takes place under action of gravity.

* * * * *